US00PP12398P2

(12) United States Plant Patent
DeJong et al.

(10) Patent No.: US PP12,398 P2
(45) Date of Patent: Feb. 5, 2002

(54) PRUNE TREE NAMED 'SUTTER'

(75) Inventors: Theodore M. DeJong, Davis; James F. Doyle, Clovis, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/536,694

(22) Filed: Mar. 28, 2000

(51) Int. Cl.[7] ..... A01H 5/00
(52) U.S. Cl. ..... Plt./185
(58) Field of Search ..... Plt./185

(56) References Cited

U.S. PATENT DOCUMENTS

PP3,862 P * 4/1976 Odier ..... Plt./185

* cited by examiner

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct cultivar of prune tree (i.e., *Prunus domestica*) is provided that resulted from a controlled breeding program. Quality early-maturing fruit is formed that is particularly well suited for the dried fruit market. The tree is regular bearing and vigorous. Dark purple fruit with a medium waxy bloom is formed that, when compared to the fruit of the 'Improved French' cultivar (non-patented in the United States), is larger, matures approximately 7 to 10 days earlier, and possesses a lighter, more complex fruity taste with a higher sugar content. The fruit stone is nearly free and machine pits well.

1 Drawing Sheet

BACKGROUND OF THE INVENTION

The new cultivar of *Prunus domestica* of the present invention was created during 1987 in the course of prune breeding research carried out at the Kearney Agricultural Center of the University of California located at Parlier, Calif. *Prunus domestica* is commonly known as the European plum. The female parent (i.e., seed plant) was the European plum cultivar 'Sugar' (non-patented in the United States) and the male parent (i.e., pollen parent) was the prune cultivar 'Primacotes' (non-patented in the United States). The parentage of the new cultivar is expressed as follows:

'Sugar'×'Primacotes'.

During the course of the breeding program over 500 crosses were attempted following emasculation. Seeds resulting from such cross-pollination were harvested at the end of the growing season. These were planted during 1988 and the resulting plants were given the group designation P88.17. The seedlings were grown in a nursery at Parlier, Calif. and were carefully studied during the remainder of 1988 and 1989. At the end of the 1989 growing season, 205 small trees were dug and were placed in cold storage. These trees were transplanted into seedling rows in the spring of 1991 and their study continued. A single tree of the new cultivar of the present invention was selected during 1993 when such seedling first fruited. This seedling initially was designated 4-6W-53.

It was found that the new *Prunus domestica* cultivar of the present invention:

(a) Exhibits a vigorous growth habit, (b) Is productive and regular bearing, and (c) Forms dark purple fruit with a medium waxy bloom capable of being dried to a high quality prune that, when compared to the fruit of the 'Improved French' cultivar, is larger, matures approximately 7 to 10 days earlier, and possesses a lighter, more complex fruity taste with a higher sugar content.

The new cultivar has been asexually reproduced by grafting and budding. During February of 1994, the new cultivar was first asexually propagated at Parlier, Calif. by grafting onto 'Marianna' plum rootstock (non-patented in the United States). The resulting tree produced a small amount of fruit in 1995 and the first significant amount of fruit in 1996. Good fruit production continued in 1997, 1998, and 1999. The fruit produced on the propagated tree was the same as that of the original seedling in all respects. The new cultivar was first grafted onto 'Myrobalan 29C' rootstock (non-patented in the United States) in 1996. Such propagation was also successful. Attempted field grafts onto peach rootstocks have resulted in scion breakage at the graft union. Accordingly, at the present time, peach rootstocks are not recommended. The new cultivar was found to reproduce true to form via such asexual propagation using 'Marianna' and 'Myrobalan' rootstock and performed well on such rootstocks in all respects.

The new cultivar has been further evaluated at test sites in the San Joaquin and Sacramento Valleys of California. These tests have further confirmed the commercial potential of the new cultivar.

In a typical year, the fruit of new cultivar commonly reaches maturity during early to mid-August at Parlier, Calif. This is approximately 7 to 10 days earlier at such location than that produced on the most commonly grown 'Improved French' prune cultivar (non-patented in the United States). Accordingly, the new cultivar can be grown to advantage in conjunction with the 'Improved French' cultivar so that harvest and processing season at a given location can be extended. The fruit shape resembles that of the 'Improved French' cultivar, but commonly is approximately 15 to 20 percent larger. Also, the fruit of the new cultivar commonly develops at least 2 degrees Brix soluble solids more than the 'Improved French' cultivar at full maturity. Limited tests with mechanical harvesting of the fruit have been successful with very little fruit damage.

When the new cultivar of the present invention is compared to the 'Sugar' parent, there are distinct differences in areas of fruit shape, fruit color, fruit size, stone shape, stone size and adhesion, production characteristics, and tree form. The fruit of the 'Sugar' cultivar is oval in form and reddish to reddish-purple in coloration. In contrast the fruit of the new cultivar is pyriform in shape with a broad but distinct neck and is dark purple-red to dark purple-blue in coloration. The fruit of the 'Sugar' cultivar is medium in size and about 10 percent larger than the industry standard 'Improved French' cultivar in an average to light-set year. The fruit of the new cultivar is medium to large in size and commonly 15 to 20 percent larger than that of the 'Improved French' cultivar. The stone of the 'Sugar' prune is large and commonly has a large protruding wing along the basal suture area. This wing can lead to the presence of excessive pit fragments in mechanically pitted dried fruit. The stone of the new cultivar is smaller than that of the 'Sugar' cultivar and possesses no wing or other protrusion. The stone of the 'Sugar' cultivar also is a clingstone and tightly adheres to the fruit flesh. The 'Sugar' cultivar is decidedly alternate bearing. The new cultivar has little tendency to alternate bear. The trees of the 'Sugar' cultivar are very open in form with less tree density then either the 'Improved French' cultivar or the new cultivar of the present invention. The date of maturity for the prunes of the 'Sugar' cultivar commonly ranges from approximately five days to a week before that of the presently claimed cultivar.

It will be further noted that substantial differences exist between the new cultivar and the 'Primacotes' parent with regard to fruit color, the distribution of fruit on the tree, the date of maturity, the soluble solids content of the fruit, tree productivity, and sensitivity to heat. The fruit of the 'Primacotes' cultivar is reddish to reddish-purple in coloration and is primarily borne in large clusters towards the ends of the previous season's shoots. This reuslts in lower productivity. The fruit of the new cultivar is borne throughout the tree and as indicated is dark purple-red to dark purple-blue in coloration. In California the fruit of the 'Primacotes' cultivar commonly ripens approximately two weeks ahead of the 'Improved French' cultivar. At full maturity the 'Primacotes' cultivar commonly develops a fruit soluble solids level of no more than 22 degrees Brix while that of the new cultivar commonly averages 24 Brix or above. When grown in the hot interior San Joaquin Valley of California, the 'Primacotes' cultivar often displays a moderate amount of internal heat damage to the fruit. Such heat damage has never been observed in the new cultivar under the same growing conditions.

The pollination requirements for the new cultivar are not fully known to date. Limited tests indicate that the variety is at least partially self-fruitful. Fruit set may be enhanced by the use of a pollinator. Limited tests indicate that the 'Improved French' cultivar having a bloom date which well corresponds to that of the new cultivar can serve as a pollinator.

The disease resistance/susceptibility of the new cultivar based on field observations appears to be substantially the same as that of the 'Improved French' cultivar during observations to date. Such observations have been made primarily with respect to Brown Rot, the principle fungal disease found in prunes in California.

The new cultivar of the present invention is particularly well-suited for the dried fruit market. The fruit stone is nearly free and machine pits well. Also, the new cultivar is a candidate for the fresh fruit market. Currently the fresh prune crop produced in the United States is largely exported to Pacific Rim countries where it is held in particularly high regard. The smaller size commonly exhibited by fruit sold in the fresh fruit market may limit this end use. In particularly heavy crop years where size is further diminished, the possibility of usage in the fresh fruit market likely will be further diminished.

The new cultivar has been named 'Sutter'.

BRIEF DESCRIPTION OF THE PHOTOGRAPH

The accompanying photograph shows typical specimens of the foliage (both surfaces), fruit (with and without the epidermal bloom), fruit flesh, and pit of the new cultivar as depicted in color as nearly true as it is possible to make the same in a color illustration of this character. The tree of the new cultivar was grown at the Kearney Agricultural Center of the University of California at Parlier, Calif. The fruit shown in the photograph was harvested during early to mid-August and was at near full commercial maturity. Dimensions in centimeters are shown at the bottom of the photograph.

DETAILED DESCRIPTION

The following is a detailed description of the new prune tree cultivar that was obtained from the observation of six year-old asexually propagated trees during the 1999 growing season except where otherwise indicated. The trees were propagated on 'Marianna' plum rootstock. The trees were grown at the Kearney Agricultural Center of the University of California located at Parlier, Calif. Tree spacing was 5.49 m between rows and 4.88 m spacing between trees in the row. The color chart used in the identification of colors is that of The Royal Horticultural Society, London (R.H.S. Colour Chart). Other color terminology is to be accorded its customary dictionary significance.

Botanical classification: *Prunus domestica,* cv. 'Sutter'.

*Female parent.*—cv. 'Sugar'.

*Male parent.*—cv. 'Primacotes'.

Tree:

*Size.*—The height of a tree pruned into an open-vase training system at the end of the growing season ranges from approximately 5.5 to 5.7 m including approximately 1.5 to 2.0 m of current season's growth. The width across the crown ranges from approximately 4.2 to 4.4 m.

*Vigor.*—Good.

*Growth.*—Upright-spreading.

*Hardiness.*—Hardy under typical San Joaquin Valley of California climatic conditions.

*Production.*—Good fruit productivity.

*Bearing.*—Regular Bearer.

Trunk:

*Size.*—The lower 1 m of the trunk was 'Marianna' rootstock. At 45 cm above the ground, the 'Marianna' trunk measures 14 cm in diameter. The varietal top was composed of 3 scaffolds having diameters at the graft unions of 11.5, 12.5 and 13.5 cm.

*Texture.*—The scaffold surface is moderately roughened with a moderate quantity of scarfskin.

*Color.*—Greyed-Green Group 197A to Brown Group 200C.

*Lenticels.*—Numerous, oval and somewhat flattened in configuration with a calloused surface. The height commonly ranges from approximately 1 to 2 mm and the width from approximately 3 to 9 mm. The coloration is near Greyed-Orange Group 174B.

Branches:

*Size.*—Generally average in diameter for *Prunus domestica.* Typical diameters for eight year-old trees are approximately 10.0 to 14.5 at the base of primary scaffolds (average approximately 12.5 cm), approximately 4.8 to 7.1 cm at the base of secondary scaffolds (average 5.8 cm), variable and approximately 9 to 29 mm for the base of fruiting hanger limbs, and variable and approximately 3 to 6 mm at the base of fruiting spurs.

*Surface.*—Two year old and older branches have a somewhat netted surface and are somewhat rough. Older shoot surfaces are essentially glabrous and younger current season's shoots are moderately pubescent. Numerous short stiff hairs are present on the young shoot surface.

*Color.*—Mature one year-old shoots are medium brown of Greyed-Orange Group 175B. Immature shoots are light green of Yellow-Green Group 145A. Young shoots exposed to the direct sunlight can take on various hues of rose to red. New expanding shoot tips commonly are bright yellow-green of Yellow-Green Group 151B. Two year-old or older wood commonly is brownish-green near Grey-Brown Group 199B to darker grey of Greyed-Green Group 197A.

*Lenticels.*—Substantial presence on the trunk and large scaffolds. Commonly possess a calloused surface and range in size from approximately 3 to 9 mm in length and approximately 1 to 4 mm in width. The color is light brown, Greyed-Brown Group 174B.

*Internode length.*—Within the normal range for *Prunus domestica.* The distance between nodes commonly ranges from approximately 27 to 44 mm on one year-old hanger wood.

Leaves:

*Size.*—Generally are medium in size. Leaves produced near mid-shoot on vigorous current season's shoots range in length from approximately 11.1 to 13.4 cm including the petiole and in width from approximately 5.2 to 6.4 cm. The thickness is normal and the surface is moderately rugose.

*Form.*—Variable, from oval to obovate. The leaf apices are acute and at times are slightly reflexed sideways. The leaf base is cuneate. With advancing maturity, some older leaves are folded downwards from the midrib.

*Color.*—The upper surface is dark green, Yellow-Green Group 147A. The under surface is lighter green, Yellow-Green Group 147C. The primary mid-vein on the under surface is pale green, Yellow-Green Group 145C. The lower leaf surfaces are sparsely pubescent and the surfaces of the lower veins are highly pubescent.

*Margin.*—Crenate and at times doubly crenate. The crenations tend to be relatively large and moderately irregular. The margins are moderately undulate.

*Venation.*—Pinnate.

*Petiole.*—Average in size, commonly approximately 18 to 28 mm in length, approximately 1.5 to 2 mm in diameter, and light yellow-green, Yellow-Green Group 145B, in coloration. The petiole surface is highly pubescent.

*Glands.*—From 1 to 2 very small globose glands commonly can be observed on the tip of two serrations located at the very base of the leaf margin. The serrations with glands are alternate in position. Most frequently no glands are present on the petiole stalk. The coloration when young is bright yellow-green, Yellow-Green Group 149A, with darkening and deterioration with age.

*Stipules.*—Medium to large in size, linear lanceolate in configuration, frequently partially deciduous with some stipules remaining on the leaf throughout the growing season, margins are serrate, commonly approximately 6 to 12 mm in length at full maturity, and the coloration is medium green, Yellow-Green Group 144B.

Fruit:

*Maturity when described.*—Full commercial maturity.

*Picking.*—Aug. 23, 1999 and appropriately one week ahead of the 'Improved French' cultivar. Prunes typically are harvested on one date using a mechanical shaker. The 1999 fruit growing season in the San Joaquin Valley are of California was one of the latest on record and ranged from 12 to 15 days later than average. A more typical harvest date would be during the first or early second week of August. At picking time the fruit displayed on average flesh pressure of 4.1 pounds and an average soluble solids content of 24.0 degrees Brix.

*Size.*—Generally large for a prune and relatively uniform in size. Cheek diameter ranges from approximately 29 to 34 mm, suture diameter from approximately 30 to 36 mm, and axial diameter from approximately 47 to 51 mm.

*Form.*—Pyriform in lateral aspect, from oval to nearly globose in apical aspect, and varies from nearly symmetrical to slightly asymmetrical.

*Suture.*—Very slightly indented and extends fully from the fruit base to apex, and varies from approximately 1 to 1.25 mm in width. Usually no stitching or callousing is present. The suture color is variable and usually is very slightly darker than the color of the surrounding skin surface. The suture color range from red-purple, Greyed-Purple Group 184B, to dark purple-burgundy, Greyed-Purple Group 187A.

*Ventral surface.*—Relatively smooth with almost no lipping.

*Stem cavity.*—Very small and so shallow that at times it appears to be non-existent. The length commonly averages from approximately 4 to 7 mm, the width commonly ranges from approximately 4 to 6 mm, and the depth commonly ranges from 0.5 to 2 mm. The cavity form is oval to nearly globose.

*Base.*—Somewhat narrow and tapered to a slightly truncate in form. The base angle is strongly oblique to the fruit axis. This attachment gives the stem the appearance of being attached to the upper lateral surface of the fruit.

*Apex.*—Usually rounded and only occasionally very slightly depressed. The pistil point is apical and most frequently takes the form of a small calloused dot.

*Stem.*—Somewhat thickened at the distal end. The surface is pubescent with a substantial number of short bristly hairs present throughout the surface of the stem. The length commonly ranges from approximately 10 to 19 mm. The diameter commonly ranges from 1 to 2 mm. The color is pale green at commercial maturity, near Yellow-Green Group 148C with some slight brown coloration, Grey-Brown Group 199C, at times. The stem attachment is below the highest point of the base.

*Skin pubescence.*—Glabrous.

*Skin thickness.*—Average.

*Skin flavor.*—Relatively neutral.

*Skin tendency to split.*—No tendency to crack or split has been observed.

*Skin tenacity.*—Tightly attached to the flesh at commercial maturity.

*Skin color.*—Highly colored over 95 to 100 percent of the fruit surface. Light bluish grey, Violet-Blue Group 98D, to more violet-grey, Greyed-Purple Group 185C, at commercial maturity when the waxy cuticle bloom is intact. Once the bloom is removed the coloration is purple-red, Greyed-Purple Group 184B, to dark purple-blue, Purple Group 79A. An amber-yellow ground color, Yellow-Orange Group 20A, covers 5 percent or less of the fruit surface. Such ground color (if present) is most frequently at the basal end of the fruit. Numerous light-colored dots are often present throughout the skin surface. Such dots commonly are of the same color as the ground color indicated above.

*Flesh color.*—The interior flesh is relatively uniform from amber-yellow, Yellow-Orange Group 20A, to slightly darker amber-buff, Yellow Orange Group 22A. Such darker coloration appears primarily at the stone cavity. Some short and fine fibers are visible in the flesh that typically are light yellow in coloration.

*Flesh texture.*—The firmness holds very well on the tree. At commercial maturity the flesh is firm, crisp and juicy. The flesh texture is fine and relatively dense.

*Ripening.*—Ripens evenly throughout.

*Flavor.*—Rich and well-balanced. The dried fruit is high in sugar content with mild acidity and a fruity character. Typical fully ripened fruit in the 3 to 4 pound pressure range displayed average soluble solids readings in degrees Brix of 25.2 to 1997, 23.6 in 1998 and 24.0 in 1999.

*Aroma.*—Very slight and pleasing.

*Eating quality.*—Excellent.

*Processing quality.*—In testing to date the fruit was 15 to 20 percent larger in size than that of the 'Improved French' cultivar. At full maturity, the soluble solid content is at least 2 degrees Brix higher than that of the 'Improved French' cultivar for an equal crop load and similar location. The fruit stone is nearly freestone and mechanically pits easily. Limited tests with mechanical harvesting of fruit were successful with minimal fruit damage being observed. The fruit dries to a very high quality prune. The external appearance of the dried product is similar to that of the 'Improved French' cultivar. The flavor is lighter with a sweeter more complex fruity taste.

Stone description:

*Attachment.*—Various from full freestone to slightly attached to the flesh along the suture edges.

*Size.*—Medium, commonly ranges from approximately 25 to 29 mm in length, approximately 10 to 12 mm in width, and approximately 6 to 8 in thickness.

*Fibers.*—A few short fibers are present, either attached to the suture edges or on the basal neck.

*Form.*—Variable from a slightly irregular narrow oval to slightly obovate.

*Base.*—Relatively narrow and somewhat truncate and distinctly oblique to the fruit axis.

*Hilum.*—Small and commonly averages approximately 1.5 to 2 mm in length and from 1 to 1.5 mm in width. Is oval and substantially eroded. The basal neck under the hilum is substantially ridged and grooved. The ridges converge basally.

*Apex.*—Usually rounded with only an occasional low tip. The apex shoulder is moderately eroded on the dorsal suture side of the apex.

*Sides.*—Variable and range from equal to slightly unequal.

*Surface.*—Relatively smooth laterally with only very slight surface roughening, and grooved and ridged basally over the surface of the basal neck converging basally. No significant pitting or grooving is present over the lateral surfaces.

*Ventral edge.*—Relatively broad and smooth, varies from approximately 3 to 5 mm in width at mid-suture, and the surface is shallowly grooved with very low to almost no wings being observed.

*Dorsal edge.*—A distinct and relatively wide continuous groove commonly is present along the dorsal edge from the base to approximately 3 to 4 mm of the apex. Within the upper approximately 3 to 4 of the dorsal edge just below the apex the dorsal groove narrows. The doral shoulder is moderately eroded.

*Color.*—When dry, light chamois, Greyed-Orange Grouup 165C. When wet, darker brown, Greyed-Orange Group 165B.

*Tendency to split.*—None observed.

Flowers:

*Chilling season.*—Data for this description was obtained during March 1999. There were approximately 1331 chilling hours below 45° F. for the 1998–1999 winter season.

*Floral buds.*—Range from small to medium in size, conic in form, normally plump, relatively free from the bearing stem, and hardy under typical San Joaquin Valley climatic conditions. The bud surface scales are medium brown, Greyed-Orange Group 176A, in coloration, are generally glabrous with margins that are somewhat serrated and pubescent. The number of buds per node can range from approximately 2 to 6 and most commonly is approximately 4. Such buds commonly are present in abundance.

*Blooming time.*—Average for the species. Full bloom occurred on approximately March 28th during 1999. This was identical to the 'Improved French' cultivar under the same conditions. The duration of the bloom was approximately 7 to 8 days, and slightly longer than that of the 'Improved French' cultivar. Frequently the new cultivar blooms 1 to 2 days earlier and finishes blooming 1 to 2 days later than the 'Improved French' cultivar. The date and duration of bloom can be substantially impacted by the number of chilling hours received in a specific year. The 1999 growing season developed later than a typical year. A more normal date of full bloom would be approximately 10 days earlier. For instance, the full bloom date for 1997 was March 19th.

*Size.*—Medium for the species. The fully expanded flower diameter commonly is approximately 22 to 27 mm.

*Bloom quantity.*—Abundant.

*Petals.*—Medium in size and commonly range from approximately 10 to 13 mm in length and approximately 7 to 9 mm in width. The number is 5 per flower. The form varies from oval to at times somewhat obovate. The petals at full maturity are often cupped inwards. The coloration is white, White Group 155B. The petal claw or petal base is medium in size, averages 1.5 cm in width, is glabrous, and is tapered basally with a truncate base. The margins are relatively smooth to slightly undulate. The apices are generally rounded and at times with a ruffled margin at the apex.

*Pedicel.*—Commonly approximately 10 to 13 mm in length and a diameter of approximately 1 mm measured at the mid-point. The coloration is light green, Yellow-Green Group 144C, and the surface is highly pubescent with short, light-colored, somewhat bristly pubescence.

*Nectaries.*—Green, Yellow-Green Group 152D, and becoming darker with age, Yellow-Green Group 152C.

*Calyx.*—Pubescent with short bristly pubescence, and light green in coloration, Yellow-Green Group 145B, with darker coloration at the calyx veins, Yellow-Green Group 144B.

*Sepals.*—Five in number, the surface characteristics of central area are variable from fully glabrous to slightly pubescent, and the margins are highly pubescent. The size is average, approximately 4 to 5 mm in length and approximately 2 to 3 in width, the form is variable and most frequently is ovate and strongly cupped inwards, and the coloration is light green, Green Group 145B.

*Anthers.*—Average in size, and bright yellow-gold, Yellow Group 13A, both ventrally and dorsally in coloration.

*Pollen.*—Abundant and yellow-gold, Yellow-Orange Group 14B, in coloration.

*Stamens.*—Length is variable and commonly approximately 7 to 12 mm, and commonly the height is slightly shorter than the pistil at the full expansion. The color is white, White Group 155B.

*Pistils.*—Usually glabrous with hairs being sparsely present. The style is usually completely glabrous. The length including the ovary is approximately 10 to 15 mm. The pistil basal area including the ovary is green, Yellow-Green Group 144C. The style area is lighter green, Yellow-Green Group 145C to 145D.

We claim:

1. A new and distinct cultivar of *Prunus domestica* tree exhibiting the following combination of characteristics:

(a) exhibits a vigorous growth habit, (b) is productive and regular bearing, and (c) forms dark purple fruit with a medium waxy bloom capable of being dried to a high quality prune that, when compared to the fruit of the 'Improved French' cultivar, is larger, matures approximately 7 to 10 days earlier, and possesses a lighter, more complex fruity taste with a higher sugar content; substantially as herein shown and described.

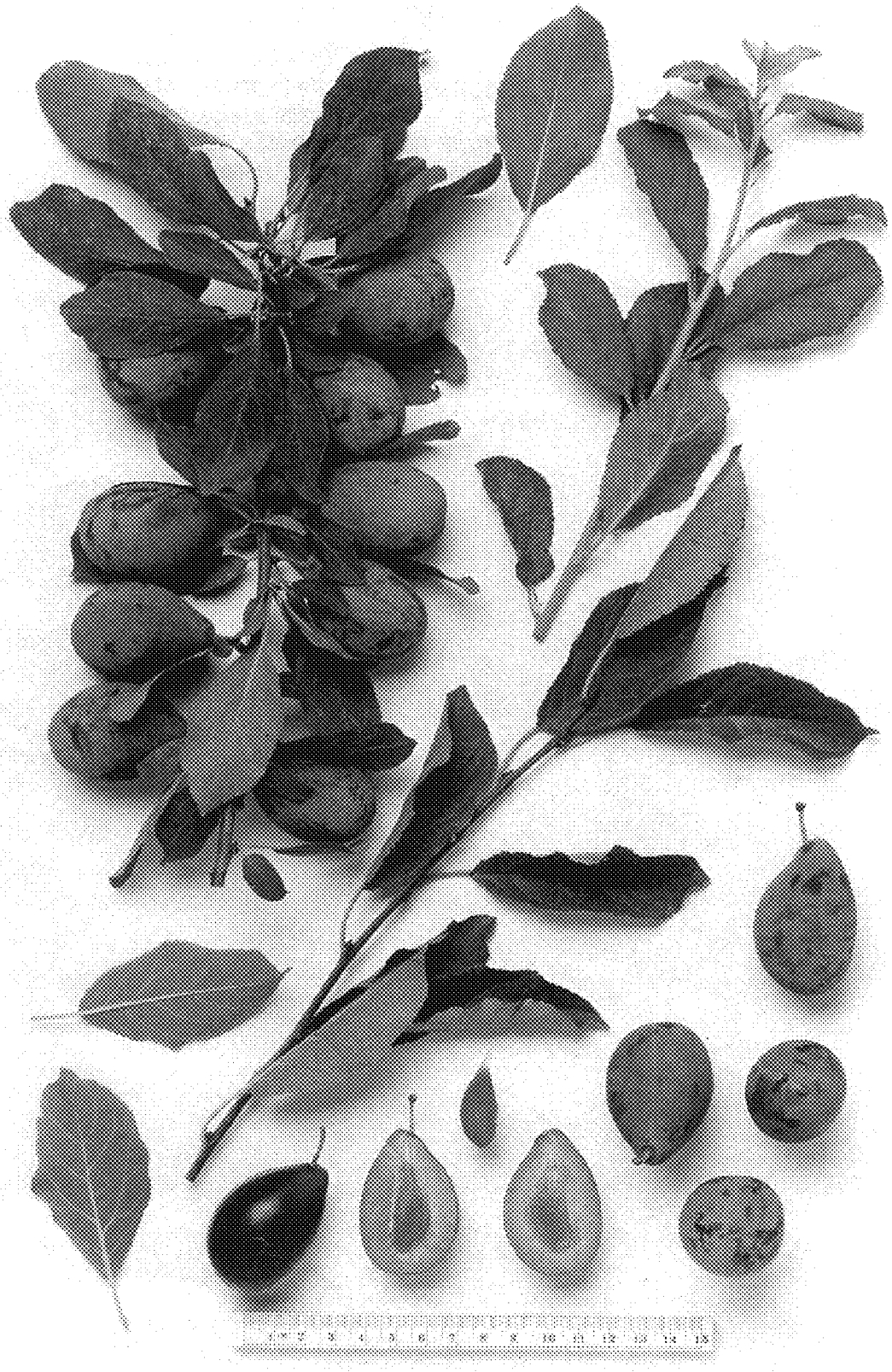

* * * * *